United States Patent [19]

Trouet et al.

[11] 4,388,305

[45] Jun. 14, 1983

[54] VINBLASTIN-23-OYL AMINO ACID DERIVATIVES FOR USE AS ANTITUMOR AGENTS

[75] Inventors: André B. L. Trouet, Winksele; Jean A. A. J. Hannart, Dion Valmont; Kandukuri S. B. Rao, Rosières, all of Belgium

[73] Assignee: Omnichem S.A., Belgium

[21] Appl. No.: 269,876

[22] Filed: Jun. 3, 1981

[30] Foreign Application Priority Data

Jun. 10, 1980 [LU] Luxembourg .......................... 82514
Dec. 23, 1980 [LU] Luxembourg .......................... 83034

[51] Int. Cl.³ .................. A61K 31/475; C07D 519/04
[52] U.S. Cl. ............................ 424/177; 260/112.5 R; 260/244.4; 424/262
[58] Field of Search .................... 260/112.5 R, 244.4; 424/177, 262

[56] References Cited

U.S. PATENT DOCUMENTS 3,387,001 6/1968 Hargrove ......................... 260/244.4
4,203,898 5/1980 Cullinan et al. .................. 260/244.4

FOREIGN PATENT DOCUMENTS 2739443 3/1978 Fed. Rep. of Germany ... 260/244.4

*Primary Examiner*—Donald G. Daus
*Assistant Examiner*—Diana G. Rivers
*Attorney, Agent, or Firm*—Ostrolenk, Faber, Gerb & Soffen

[57] ABSTRACT

Amino acid derivatives of vinblastine, including peptide derivatives, methods of their preparation and pharmaceutical compositions containing such vinblastine derivatives for use as antitumor agents are described.

17 Claims, No Drawings

VINBLASTIN-23-OYL AMINO ACID DERIVATIVES FOR USE AS ANTITUMOR AGENTS

FIELD OF THE INVENTION

This invention relates to novel bisindole alkaloids. More particularly, the invention relates to amino acid derivatives of vinblastine, including peptide derivatives, to methods for their preparation, and to pharmaceutical compositions containing such vinblastine derivatives as antitumor agents, and particularly for use in treating malignant tumors in humans.

REPORTED DEVELOPMENTS

Bisindole alkaloids of the vinblastine type are well-known compounds of the general formula:

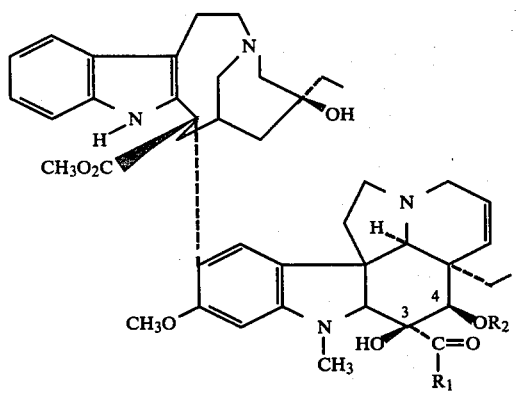

(I)

Such alkaloids include vincaleukoblastine (U.S. Pat. No. 3,097,137), leurocristine or vincristine and leurosidine (U.S. Pat. No. 3,205,220), vinglycinate (Belgian Pat. No. 659,112) and vindesine (Belgian Pat. No. 813,168). The latter compound is obtained by chemical modification of natural vinblastine (I, $R_1=OCH_3$, $R_2=COCH_3$), which is obtainable by extraction from Catharanthus roseus leaves.

Vinblastine, vincristine and vindesine are commercially available for use in human therapy, more particularly, for the treatment of leukemia and some solid tumors.

However, these drugs have been shown to possess major unfavorable side-effects. Vincristine shows neurotonic effects and vinblastine is considered to have potent bone marrow depressant effects, i.e. hematopoietic toxicity.

The mechanism of action of these drugs is believed to be similar to the mechanism which has been postulated for the antimitotic action of colchicine. In such case, these drugs would act through inhibition of the polymerization of tubuline to give microtubules, and subsequent arrest of the cell cycle at the mitotic phase.

The utilization of 1:1 complexes of tubuline with antitumoral bisindole alkaloids has been described in Belgian Pat. No. 854,053. In some cases, lower toxicity and more efficient chemotherapeutic activity than free alkaloids was reported.

Various other chemical modifications of the vinblastine molecule have been tested. One of these modifications, vinglycinate sulphate (I, sulphate, $R_1=OCH_3$, $R_2=COCH_2N(CH_3)_2$ (Cancer Research 1967,27,221–227), has also been tested clinically but has been shown to be generally not superior to vinblastine or vincristine.

Belgian Pat. No. 813,168 discloses Vindesine (I,R,=$NH_2$, $R_2$=H) and vinblastine carboxamide derivatives. Subsequent reports indicate that in spite of general usefulness of vindesine or 3-carboxamide 4-O-deacetyl vinblastine, they are not efficient for the treatment of mouse induced murine 1210 leukemia (C. J. Barnett et al., J.Med.Chem. 21,88,1978). Vindesine is currently sold on the European market (i.a. in France and Germany) and FDA registration is pending in the U.S.A.

Amino acid derivatives of vinblastine or other bisindole alkaloids have been proposed generally in Belgian Pat. No. 813,168. However, no specific amino acid derivatives are disclosed and consequently, no physicochemical descriptions, no specific method of preparation and no particular physico-chemical properties are disclosed. It may thus be assumed that such compounds have not been actually synthesized and/or have not been tested for their antimitotic potencies, particularly in view of the statement in the disclosure at page 3, line 10 et seq. that "anti-neoplastic activity seems to be limited to very specific structures, and the chances of obtaining more active drugs by modification of these structures would seem to be correspondingly slight".

It has now been found that the new compounds according to this invention are able to substantially delay the death of mice inoculated intravenously with P 388 and L 1210 leukemias and show important advantages over the previously described vinblastine analogs.

Vinca alkaloids generally show no activity on L 1210 leukemia. The results obtained with the new compounds of the invention indicate highly unexpected and surprising activities on P 388 and L 1210 experimental tumors. Numerous total remissions have been observed. The compounds of the instant invention further show other important and unexpected advantages compared to vinblastine and known analogs, especially vindesine. More particularly, the toxicities are generally more favorable when compared to vincristine or vindesine.

SUMMARY OF THE INVENTION

This invention involves a novel class of vinblastine derivatives particularly 23-oyl amino acid derivatives of vinblastine and 23-oyl amino acid derivatives of 4-deacetyl vinblastine, i.e. compounds of Formula I wherein $R_1$ is an amino acid ester or a peptide ester attached to the vinblastine-23-oyl moiety or the 4-deacetyl vinblastine-23-oyl moiety through an amide linkage and their pharmaceutically acceptable salts.

In another aspect, the invention involves the preparation of novel vinblastine derivatives by hydrazinolysis of vinblastine followed by nitrosation and coupling with an amino acid or polypeptide ester.

In still another aspect, the invention involves therapeutic methods and compositions for the treatment of cancers in mammalian species by administering to a cancer patient an effective amount of a compound of Formula I.

DETAILED DESCRIPTION OF THE INVENTION

The new compounds of the present invention are those of the general formula II:

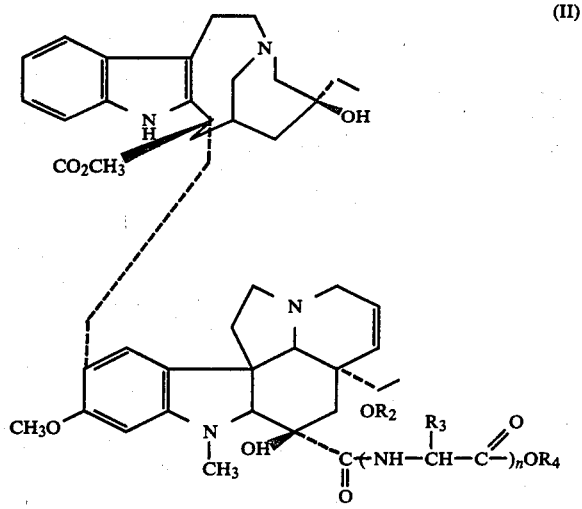

(II)

wherein $R_2$ is a hydrogen atom or $C_2$-$C_9$ acyl group, preferably acetyl; $R_3$ is a hydrogen atom, straight or branched $C_1$-$C_8$ alkyl, hydroxy-$C_1$-$C_8$-alkyl, carboxy-$C_1$-$C_8$-alkyl, amido-$C_1$-$C_8$-alkyl, amino-$C_1$-$C_8$ alkyl or hydroxyalkyl, quanadino-$C_1$-$C_8$-alkyl, thiol-$C_1$-$C_8$-alkyl, cysteinyl-methyl, methylthioethyl, benzyl, hydroxy-benzyl, or a group:

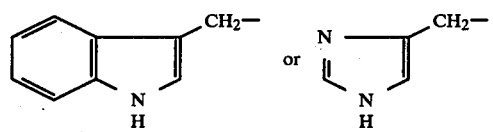

or $R_3$ together with the carbon to which it is attached and the amido nitrogen, forms an azole or hydroxy azole ring; n is an integer of from 1 to 6; and $R_4$ is a straight or branched $C_1$-$C_8$-alkyl or a α benzyl group.

—COOR$_4$ is preferably the carboethoxy or the carbomethoxy group.

In a preferred embodiment, the structural segment

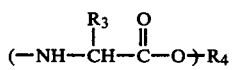

in general formula II, represents an ester derived from any of the naturally-occuring amino acids and their optical isomers of D-configuration, namely glycine, alanine, valine, leucine, isoleucine, serine, threonine, aspartic acid, glutamic acid, aspargine, glutamine, arginine, lysine, cysteine, cystine, methionine, phenylalanine, tyrosine, trypthophan, proline, histidine, hydroxylysine, hydroxyproline.

In the case of amino acids having more than one asymmetric center, both the L-allo and the D-allo forms are included.

The compounds may be designated as 3-descarbomethoxy-O-4-deacetyl vinblastine-3-carboxamide. They will however be preferably designated as N-(vinblastin-23-oyl)-aminoacids derivatives hereafter.

Particularly preferred amino acid ester compounds of general formula II are those wherein $R_2$ is hydrogen and the amino acid moieties are derived from one of the following amino-acids: L or D tryptophan, valine, isoleucine, leucine, phenylalanine and alanine.

Most preferred among these aminoacids are L-tryptophan, L-isoleucine and L-valine.

Particularly preferred peptide derivatives are those of formula II wherein n is 2 and the amino-acids are selected from the preferred L or D six amino acids indicated above in any sequence.

As far as the pharmacological properties of the compounds are concerned, it is to be expected that slight variations of the structure of the peptide backbone will yield compounds of comparable potency. In particular, the presence of non-natural α-amino-acids (for example norleucine, N-monosubstituted - amino acids or α,αdialkyl-aminoacids) will provide compounds of similar activity against a variety of tumors and are to be considered as included in the scope of the present invention.

The compounds of general formula II can be obtained starting from vinblastine, by hydrazinolysis followed by nitrosation and reaction with the appropriate amino acid ester or peptide ester.

When the amino acid or peptide moiety contains a functional side chain $R_3$ it may be necessary to protect the functional groups according to well-known methods used in peptide chemistry. This is more particularly the case for lysine or cysteine. Protection may be achieved, depending on the nature of the amino acid, by the presence of a benzyl, trifluoro-acetyl, t-butyl, benzyloxycarbonyl, t-butoxycarbonyl or trityl radical condensed with the functional group. Other well-known protecting groups in common use in peptide chemistry may successfully be used.

The compounds of the present invention may be prepared starting from vinblastine, by hydrazinolyse followed by nitrosation and reaction with the amino acid ester on the peptide in accordance with the reaction sequence hereunder.

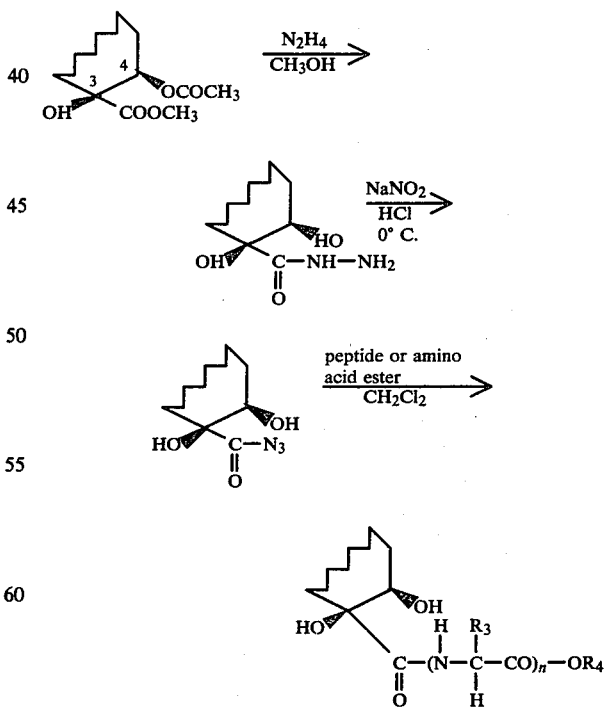

The first step of the process preferably comprises adding anhydrous hydrazine in excess to a solution of vinblastine base in anhydrous methanol. The solution is heated in an inert atmosphere ($N_2$ or Ar) for 12 to 30 hours at a temperature varying between about 30° C. and 70° C. Most preferably the temperature is maintained around 60° C., reaction time then being 24 hours.

The resulting hydrazine of 4-O-deacetyl-vinblastin-23-oic acid (I, $R_1 = NH—NH_2$, $R_2 = H$) is then isolated by adding water, extracting with a water-immiscible solvent such as methylene chloride and concentrating under reduced pressure. The compound may be further purified by column chromatography (preferably on neutral silica).

In a second step, the hydrazide group of the modified vinblastine is transformed into an acyl azide. This transformation is best achieved by adding sodium nitrite to the hydrazide dissolved in a water-acidic methanol mixture. The acid in this mixture may be, for instance, hydrochloric acid. The reaction temperature is maintained between about 0° C. and 5° C.

After extraction with a water-immiscible aprotic solvent, preferably chloroform or methylene chloride, the organic phase is separated and partially concentrated.

The acyl azide is generally not isolated but directly added to the amino acid ester or the polypeptide, or a protected derivative thereof, dissolved in a suitable solvent such as methylene chloride.

The quantity of amino acid to be used is about one to four equivalents of the vinblastine carboxazide.

The reaction mixture is typically maintained between about −3° C. and +5° C. for about 15 hours. Monitoring of the reaction is best achieved by thin layer chromatography. After completion of the reaction, the solvent may be removed under reduced pressure and the resulting product may be transformed into a sulphate salt or another suitable salt derived form a mineral or organic acid, by crystallization from a methanolic solution of the corresponding acid. The pure compound of the invention may be isolated and purified by conventional techniques of crystallization and chromatography.

If desired, the resulting 4-O-deacetyl modified vinblastine can be reacylated either directly to give the vinblastine derivative II wherein $R_2$ is $COCH_3$ (J.Med.-Chem.22, 391, 1979) or through the formation of the 3,4-diacetoxy derivative followed by a selective hydrolysis of the 3-acetoxy group in the position 3. The hydroxy group in $C_4$ may be, also esterified by other activated acid derivatives containing 1-9 carbon atoms.

The instant invention relates also to the pharmaceutical compositions, particularly for use in the treatment of human cancers, comprising one or more of the new bisindole alkaloids of the invention preferably in association with a pharmaceutical vehicle.

The compounds of this invention display particularly remarkable antitumor properties which may be applied with success in human cancer therapy.

They are for example, useful when used for the treatment of L 1210, P 388, gliomas, lymphosarcomas and other leukemias or malignant tumors. In human medicine they may be useful for the treatment of Hodgkins disease and for other solid tumors treatable with vinblastine, vincristine or vindesine. These compounds are also useful in veterinary medicine for the treatment of animal tumors.

Other therapeutical uses may also be contemplated for the new compounds of the invention, similarly to vinblastine which may be used for treating same forms of arthritis (U.S. Pat. No. 4,208,411) or to vincristine which has been shown to be active for treating psoriasis (U.S. Pat. No. 3,749,784). The anti-viral activity of bis-indole alkaloids has also been reported.

For the treatment of experimental malignancies in animals, the chemotherapeutic activities have been tested using the corresponding sulphate salts.

In the tests reported DBA 2 female mice (Strain Charles River France) were inoculated intravenously by $10^4$ leukemic cells obtained from 7 days old P 388 or L 1210 leukemic ascites. Day 0 is the day of inoculation of the tumoral cells.

The compound of the invention (sulfate form) is then injected intravenously, dissolved in a physiological saline solution (NaCl 9/1000) either using a single injection schedule (day 1) or a three injections schedule (day 1, 2 and 3). The MST (Median Survival Time), i.e. the day when half of the animals have died is calculated after the 30th day.

The value ILS (Increased Life Span) is calculated in accordance with the following formula:

$$\% ILS = \left( \frac{MST \text{ product}}{MST \text{ control}} \times 100 \right) - 100$$

The number of surviving mice after the 30th and the 60th day is also indicated.

When the doses are too toxic, the ILS percentage may become negative, i.e. non treated mice survive longer than those having been injected the anti-tumoral substance.

Under certain circumstances, some variability of the ILS may be observed depending upon the origin of the mice ($DBA_2$ France or USA).

The results which have been obtained are compared with those obtained with vinblastine (VLB), vindesine (VDS) and vincristine (VCR) in Table I. The pharmacological superiority of the compound of the present invention is demonstrated in Tables II–XI.

In Table II, results obtained with some derivatives of natural leucine are represented.

The following compounds have been tested.
VLE: ethyl N-(O-4-deacetyl-vinblastin-23-oyl)-L-leucinate
VLM: methyl N-(O-4-deacetyl-vinblastin-23-oyl)-L-leucinate.

In table III, results obtained with D-leucine derivatives, namely ethyl N-(O-4-deacetyl-vinblastin-23-oyl)-D-leucinate (VDLE) are indicated.

In table IV, results obtained with L-tryptophane derivatives are represented, namely:
V-Trypt E: ethyl N-(O-4-deacetyl-vinblastin-23-oyl)-L-tryptophanate, MST calculated for 30 and 60 days.
V-Trypt M: methyl N-(O-4-deacetyl-vinblastin-23-oyl)-L-tryptophanate.

In Table V, the activities observed with a derivative of ethyl tryptophanate, of absolute D configuration: ethyl N-(O-4-deacetyl-vinblastin-23-oyl)-D-tryptophanate (VD Trypt E) is indicated.

In tables VI–XI, results are indicated which have been obtained with the following compounds; respectively
- VAE: ethyl N-(O-4-deacetyl-vinblastin-23-oyl)-L-alaninate.
- VPE: ethyl N-(O-4-deacetyl-vinblastin-23-oyl)-L-phenylalaninate.

- VILE: ethyl N-(O-4-deacetyl-vinblastin-23-oyl)-L-isoleucinate.
- VILM: methyl N-(O-4-deacetyl-vinblastin-23-oyl)-L-isoleucinate.
- VVE: ethyl N-(O-4-deacetyl-vinblastin-23-oyl)-L-valinate
- V-Tyr E: ethyl N-(O-4-deacetyl-vinblastin-23-oyl)-L-tyrosinate
- V-Val-Trypt E: ethyl N-(O-4-deacetyl-vinblastin-23-oyl)-L-valinyl-L-tryptophanate.

TABLE I

| doses mg/kg/day | schedule (days) | number of animals | MST max 30 days | ILS % | >30 days | >60 days |
|---|---|---|---|---|---|---|
| A. VINDESIN (VDS) | | | | | | |
| P 388 | | | | | | |
| 2 | 1 | 10 | 13.6 | 27.1 | 0 | 0 |
| 3 | 1 | 10 | 14 | 30.8 | 0 | 0 |
| 4 | 1 | 10 | 14.8 | 38.3 | 0 | 0 |
| 5 | 1 | 10 | 13.8 | 30.2 | 0 | 0 |
| 6 | 1 | 10 | 14 | 32 | 0 | 0 |
| L 1210 | | | | | | |
| 3 | 1 | 20 | 8.7 | 5 | 0 | 0 |
| B. VINCRISTINE (VCR) | | | | | | |
| P 388 | | | | | | |
| 0.5 | 1 | 10 | 11.56 | 4 | 0 | 0 |
| 1 | 1 | 19 | 12.32 | 15 | 0 | 0 |
| 1.5 | 1 | 20 | 12.78 | 19 | 0 | 0 |
| 2 | 1 | 10 | 6 | −46 | 0 | 0 |
| L 1210 | | | | | | |
| 0.5 | 1 | 10 | 7.56 | 1 | 0 | 0 |
| 1 | 1 | 20 | 7.91 | 5 | 0 | 0 |
| 1.5 | 1 | 20 | 8.38 | 12 | 0 | 0 |
| 2 | 1 | 10 | 8.67 | 16 | 0 | 0 |
| C. VINBLASTINE (VLR) | | | | | | |
| P 388: | | | | | | |
| 4 | 1 | 10 | 14.6 | 36.4 | 0 | 0 |
| 6 | 1 | 10 | 15.6 | 45.8 | 0 | 0 |
| 8 | 1 | 9 | 18.5 | 72.9 | 0 | 0 |

TABLE II
DERIVATIVES OF NATURAL LEUCINE

| doses mg/kg/day | schedule (days) | number of animals | MST max 30 days | ILS % | >30 days | >60 days |
|---|---|---|---|---|---|---|
| A. VLE | | | | | | |
| P 388: | | | | | | |
| 20 | 1 | 10 | 16 | 52.4 | 2 | 1 |
| 22 | 1 | 10 | 20 | 90.5 | 4 | 1 |
| 24 | 1 | 20 | 18 | 65 | 2 | 0 |
| 26 | 1 | 10 | 17.5 | 53.5 | 1 | 0 |
| 28 | 1 | 10 | 19.6 | 71.9 | 1 | 1 |
| 30 | 1 | 10 | 21 | 84.2 | 2 | 1 |
| 34 | 1 | 10 | 6 | −48 | 2 | 1 |
| 36 | 1 | 10 | 5.4 | −53 | 1 | 1 |
| 5 | 1.2.3 | 9 | 14.5 | 25 | 0 | 0 |
| 6 | 1.2.3 | 10 | 15 | 29.3 | 0 | 0 |
| 7 | 1.2.3 | 10 | 14.2 | 24.6 | 0 | 0 |
| 9 | 1.2.3 | 10 | 5 | −56 | 1 | 1 |
| 12 | 1.2.3 | 9 | 4.8 | −59 | 0 | 0 |
| B. VLM | | | | | | |
| P 388: | | | | | | |
| 10 | 1 | 20 | 16.7 | 41 | 2 | 1 |
| 10.5 | 1 | 10 | 16.4 | 53.3 | 0 | 0 |
| 11 | 1 | 19 | 17.7 | 51 | 2 | 1 |
| 11.5 | 1 | 10 | 16.8 | 57 | 0 | 0 |
| 12 | 1 | 20 | 17.5 | 49 | 3 | 2 |
| 12.5 | 1 | 30 | 17.3 | 49 | 8 | 3 |
| 13 | 1 | 20 | 20.5 | 74 | 7 | 5 |
| 15 | 1 | 10 | 18 | 55.2 | 4 | 1 |
| L 1210: | | | | | | |
| 10.5 | 1 | 10 | 10.6 | 24.7 | 0 | 0 |
| 11.5 | 1 | 10 | 10.8 | 27 | 0 | 0 |
| 12.5 | 1 | 10 | 10 | 17.6 | 0 | 0 |

TABLE III
A. VDLE

| mg/kg/day | schedule (days) | number of animals | MST max 30 days | ILS % | >30 days | >60 days |
|---|---|---|---|---|---|---|
| P 388: | | | | | | |
| 6 | 1 | 10 | 14.7 | 26.7 | 0 | 0 |
| 8 | 1 | 10 | 17 | 46.5 | 2 | 1 |
| 10 | 1 | 20 | 28.5 | 146 | 9 | 2 |
| 12.5 | 1 | 10 | 30 | 145.9 | 6 | 3 |
| L 1210 | | | | | | |
| 9 | 1 | 10 | 10.8 | 27 | 0 | 0 |
| 10 | 1 | 10 | 11 | 29.4 | 0 | 0 |

TABLE IV

| doses mg/kg/day | schedule (days) | number of animals | MST max 30 days | ILS % | >30 days | >60 days |
|---|---|---|---|---|---|---|
| A. V Trypt E | | | | | | |
| P 388: | | | | | | |
| 20 | 1 | 10 | 11.4 | 43.9 | 0 | 0 |
| 40 | 1 | 10 | 17 | 58.8 | 5 | 4 |
| 50 | 1 | 20 | 24.5 | 117 | 9 | 5 |
| 55 | 1 | 60 | 41 | 279 | 39 | 25 |
| 60 | 1 | 100 | 33 | 202 | 57 | 36 |
| 65 | 1 | 29 | 22.75 | 114 | 13 | 9 |
| 70 | 1 | 20 | 6.5 | −39 | 8 | 5 |
| L 1210: | | | | | | |
| 55 | 1 | 30 | 11.8 | 56 | 0 | 0 |
| 60 | 1 | 30 | 12.5 | 65 | 2 | 2 |
| 65 | 1 | 30 | 12 | 62 | 0 | 0 |
| 70 | 1 | 10 | 12.3 | 61.8 | 1 | 1 |
| P 388 (max 60 days): | | | | | | |
| 55 | 1 | 30 | 60 | 457 | 28 | 16 |
| 60 | 1 | 60 | 36 | 224 | 52 | 24 |
| B. V Trypt M | | | | | | |
| P 388: | | | | | | |
| 30 | 1 | 10 | 15 | 33.9 | 0 | 0 |
| 40 | 1 | 10 | 16 | 42.8 | 0 | 0 |
| 50 | 1 | 10 | 23.5 | 199.8 | 1 | 0 |
| 60 | 1 | 20 | 26 | 140 | 7 | 2 |
| 70 | 1 | 10 | 26 | 145.3 | 5 | |
| 1210 | | | | | | |
| 50 | 1 | 10 | 11.5 | 47.4 | 0 | 0 |
| 55 | 1 | 10 | 12.5 | 60.2 | 0 | 0 |

TABLE V
VD Trypt E

| doses mg/kg/day | schedule (days) | number of animals | MST max 30 days | ILS % | >30 days | >60 days |
|---|---|---|---|---|---|---|
| 20 | 1 | 10 | 13.3 | 18.7 | 0 | 0 |
| 30 | 1 | 10 | 15.8 | 41.4 | 1 | 0 |
| 40 | 1 | 20 | 16.5 | 52 | 1 | 0 |
| 50 | 1 | 10 | 22 | 107.5 | 1 | 0 |
| 60 | 1 | 10 | 4.4 | −60.7 | 1 | 0 |
| L 1210 | | | | | | |
| 40 | 1 | 10 | 9.5 | 21.8 | 0 | 0 |
| 45 | 1 | 10 | 10.5 | 34.6 | 0 | 0 |

TABLE VI
VAE

| doses mg/kg day | schedule (days) | number of animals | MST max 30 days | ILS % | >30 days | >60 days |
|---|---|---|---|---|---|---|
| P 388: | | | | | | |
| 5 | 1 | 10 | 14.8 | 27.6 | 0 | 0 |
| 10 | 1 | 10 | 16.3 | 40.5 | 0 | 0 |
| 12.5 | 1 | 19 | 16.2 | 44 | 1 | 1 |
| 15 | 1 | 20 | 17 | 46 | 5 | 4 |
| 25 | 1 | 10 | 19 | 63.8 | 2 | 1 |
| L 1210: | | | | | | |

TABLE VI-continued

VAE

| doses mg/kg day | schedule (days) | number of animals | MST max 30 days | ILS % | >30 days | >60 days |
|---|---|---|---|---|---|---|
| 12.5 | 1 | 20 | 10.4 | 48 | 0 | 0 |

TABLE VII

A. VPE

| doses mg/kg day | schedule (days) | number of animals | MST max 30 days | ILS % | >30 days | >60 days |
|---|---|---|---|---|---|---|
| P 388: | | | | | | |
| 10 | 1 | 10 | 13 | 12.1 | 0 | 0 |
| 20 | 1 | 10 | 14.4 | 24.1 | 0 | 0 |
| 40 | 1 | 10 | 30 | 158.6 | 7 | 7 |
| 50 | 1 | 30 | 13.6 | 26 | 10 | 7 |
| 55 | 1 | 10 | 14.6 | 36.4 | 1 | 0 |
| L 1210 | | | | | | |
| 70 | 1 | 20 | 8.7 | 13 | 0 | 0 |
| 75 | 1 | 10 | 9.5 | 25 | 0 | 0 |

TABLE VIII

| doses mg/kg day | schedule (days) | number of animals | MST max 30 days | ILS % | >30 days | >60 days |
|---|---|---|---|---|---|---|
| VILE | | | | | | |
| P 388: | | | | | | |
| 8 | 1 | 30 | 30 | 172 | 20 | 2 |
| 9 | 1 | 20 | 30 | 179 | 12 | |
| L 1210 | | | | | | |
| 8 | 1 | 20 | 11.57 | 58 | 0 | 0 |
| 9 | 1 | 10 | 12.8 | 68.4 | 0 | 0 |
| VILM | | | | | | |
| P 388: | | | | | | |
| 3 | 1 | 10 | 16.4 | 41.3 | 0 | 0 |
| 5 | 1 | 29 | 18.2 | 68 | 8 | 3 |
| 6 | 1 | 69 | 23.4 | 115 | 25 | 6 |
| 7 | 1 | 30 | 30 | 177 | 16 | 5 |
| 9 | 1 | 10 | 6 | −48.3 | 4 | 4 |
| L 1210 | | | | | | |
| 6 | 1 | 29 | 11.2 | 60 | 0 | 0 |

TABLE IX

VVE

| doses mg/kg day | schedule (days) | number of animals | MST max 30 days | ILS % | 30 days | 60 days |
|---|---|---|---|---|---|---|
| P 388: | | | | | | |
| 5 | 1 | 10 | 13.6 | 17.2 | 0 | 0 |
| 10 | 1 | 10 | 17.8 | 53.4 | 0 | 0 |
| 12.5 | 1 | 10 | 21 | 82.6 | 2 | 0 |
| 14 | 1 | 20 | 21 | 98 | 3 | |
| 15 | 1 | 39 | 23.5 | 107 | 14 | 4 |
| 17.5 | 1 | 9 | 8.4 | −22.2 | 0 | 0 |
| L 1210 | | | | | | |
| 15 | 1 | 19 | 11.4 | 61.9 | 0 | 0 |

TABLE X

V Tyr E
P 388

| doses mg/kg day | schedule (days) | number of animals | MST max 30 days | ILS % | 30 days | 60 days |
|---|---|---|---|---|---|---|
| 20 | 1 | 10 | 13.9 | 29.9 | 0 | 0 |
| 40 | 1 | 10 | 16.4 | 53.3 | 1 | 1 |
| 50 | 1 | 10 | 16 | 49.5 | 1 | 1 |
| 60 | 1 | 10 | 16 | 49.5 | 3 | 2 |
| 70 | 1 | 10 | 5.4 | −49.5 | 0 | 0 |

TABLE XI

V—Val—Trypt E
P 388:

| doses mg/kg day | schedule (days) | number of animals | MST max 30 days | ILS % | >30 days | >60 days |
|---|---|---|---|---|---|---|
| 15 | 1 | 10 | 26 | 132.1 | 3 | 0 |
| 25 | 1 | 10 | 27.5 | 145.5 | 3 | 2 |
| 35 | 1 | 19 | 27.5 | 154 | 8 | 4 |
| 45 | 1 | 20 | 30 | 180 | 13 | 7 |
| 50 | 1 | 19 | 27.5 | 149 | 9 | 7 |

TABLE XII intraperitoneal injected P 388
BDF 1 Charles River France female

| PRODUCT | DOSE | SCHEDULE | No OF ANIMALS | MST | ILS | 30 DAYS |
|---|---|---|---|---|---|---|
| VCR | 2.7 | 1 | 11 | 15.6 | 64.2 | 0 |
| V—Trp—E | 50 | 1 | 10 | 22 | 131.6 | 1 |
| V—Trp—E | 60 | 1 | 10 | 31 | 226 | 6 |
| V—Trp—E | 80 | 1 | 10 | 21.5 | 126.3 | 0 |

Activity of V-Trp-E and VCR on P 388 leukemia i.p inoculated in BDF 1 female mice which have received $10^6$ leukemia cells at day 0. At day 1, the active products are i.p. administrated at the given doses.

Lewis Lung Carcinoma (3LL)

$1.1 \times 10^6$ tumoral cells are intramuscularly inoculated in the right hind leg of C57B1 female mice.

The drugs are administered intravenously in a schedule of 3 injections.

The animals are killed the 23rd day after the inoculation. The weight of the primary tumor is measured in grams; the pulmonary metastasis are computed and their diameter has been measured. The weight of metastasis has been evaluated by assuming that they are spheres of density equal to 1; the number of mice without metastasis has also been indicated.

The results appear in Table XIII. The three products show an activity on the primary tumor.

The medium weight of the metastasis, their mean number as well as the number of mice without metastasis are indicated and allow an evaluation of the antimetastasic activity of the administered anti-tumoral compounds.

TABLE XIII

| Product | Dose mg/kg/day | Number of dissected mice | Weight of the tumor (g) X | Weight of the tumor (g) σ | Weight of metastasis (mg) X | Weight of metastasis (mg) σ | Mean number of metastasis | Number of mice without metastasis |
|---|---|---|---|---|---|---|---|---|
| — | — | 20 | 9.64 | 0.916 | 27.61 | 54.53 | 28.4 | 15.22 | 0 |
| VDS | 2.5 | 22 | 5.72 | 0.698 | 0.40 | 0.91 | 13.68 | 7.49 | 0 |

TABLE XIII-continued

| Product | Dose mg/kg/day | Number of dissected mice | Weight of the tumor (g) X | Weight of the tumor (g) σ | Weight of metastasis (mg) X | Weight of metastasis (mg) σ | Mean number of metastasis | Number of mice without metastasis |
|---|---|---|---|---|---|---|---|---|
| Vtryp E | 50 | 21 | 4.83 | 0.868 | 0.047 | 0.038 | 4.58 | 2.83 | 2 |

C57B1 female mice are intramuscularly inoculated at day 0 by 1.1 × $10^6$ tumoral cells. At day 1, 8 and 15, the drugs are administrated at the indicated doses. At the 23rd day the mice are killed; the primary tumor is weighted, the pulmonary metastasis are computed and their diameter has been measured.

The antitumoral activities of Tables I–XIII confirm the unexpected efficiency of the amino-acid derivatives of the present invention. Most of the compounds appear to be superior to vindesine for i.p. and i.v. inoculated tumors. The exceptional activity of these compounds on L 1210 tumors has been demonstrated.

It may be worth mentioning that among experimental tumors presently available, L 1210 leukemia is recognized as being the experimental tumor which is the most significant for the selection of anti-tumor drugs for humans.

In Table XIV the anti-metastasic tests show that the VLB-Trypt-E derivative is very superior to vindesine. The efficiency on a primary tumor is further comparable to vindesine.

The outstanding activity of the ethyl N-(deacetyl-O-4 vinblastin-23-oyl) tryptophanate sulphate which gives a ILS after 60 days (P 388) of 457% with half of the mice surviving more, should be mentioned. The optimal dose is about 60 mg.

Generally speaking, the compounds of the invention appeared highly less toxic than Vinca alkaloids presently used in anti-cancerous therapy. The lethal dose 50 ($LD_{50}$) of VLE have been determined on $CD_1$ female mice of the Charles River strain having a less than 24 g weight. The Litchfield and Willcoxon evaluation method gives a $LD_{50}$ of 32 mg/kg.

Corresponding doses for vinblastine and vindesine are 24 mg/kg and about 11 mg/kg, respectively. As opposed to vinblastine the absence of hepatic toxicity at doses of 20 to 40 mg/kg has been observed.

The acute toxicities of V-Trp-E and VILE have also been determined on NMRI female mice. The values which have been obtained, 100.8 mg/kg and 17.7 mg/kg for V-Trp-E and VILE respectively, are to be compared with the corresponding values of 27.4 and 13.8 mg/kg for vinblastine and vindesine, respectively. V-Trp-E is thus clearly less toxic than VLB or VDS.

In utilizing the vinblastinoyl amino acid derivatives as antineoplastic agent, either the parental or the oral route of administration may be employed. For oral dosage, a suitable quantity of a pharmaceutically acceptable salt of an amino acid derivative of formula II is mixed in an excipient and the mixture placed in capsules or compressed into tablet in association with the usual binders. However, for their therapeutical uses, compounds of the invention, possibly in the lyophilized form, are preferably administered by parenteral route, dissolved in a pharmaceutically acceptable carrier either in the form of a base or of a pharmaceutically acceptable acid addition salt. A physiological water and other saline solutions buffered, for instance, with a phosphate are appropriate solvents.

Any of the acids generally employed in preparing pharmaceutically acceptable salts may be used, such as, for example, salts with mineral acids, e.g. hydrochloric, sulfuric, orthophosphoric, etc., or salts with organic acids, e.g. alkanoic acids, citric, benzene sulfonic, toluene sulfonic, methane-sulfonic, tartric oxalic, lattice etc. .

In general, the compounds can be used in human therapy in an analogous manner to the technique and limitations in use for other Vinca alkaloids.

General method for preparing N-(deacetyl-O-4-vinblastin-23-oyl) amino-acid derivatives 1 g (1.3 $10^{-3}$M) of 3-decarbomethoxy-O-4deacetyl-vinblastin-3-carboxhydrazide are dissolved in 23 ml anhydrous methanol and 74 ml HcL 1N. The solution is then cooled at $-10°$ C. and 207 g sodium nitrite are added in one batch.

The mixture is kept for 10–30 minutes at 0° C. After monitoring by thin layer chromatography (t.l.c.) the pH of the mixture is adjusted to 8.5 at $-10°$ C. by addition of a saturated solution of sodium bicarbonate.

The alkaline solution is extracted at 0° C. by a volume of methylene chloride equal to its own volume at 0° C., till a negative Meyer reaction is obtained on the aqueous phase. The organic phases are combined, dried on $Na_2SO_4$, and filtrated at 0° C.

1.43 $10^{-3}$M (1.1. equivalent) of the intended amino-acid are added and the solution is concentrated under reduced pressure until a volume of about 4 ml is obtained. This solution is kept for 24–48 hours at 4° C. The evolution of the reaction is monitored by thin layer chromatography. The solvent is completely removed and 1.05 g of dry compound are obtained, said compound appearing as a single spot in t.l.c.

Purification

The dried product above is purified in a silicagel column, the elution agent being a mixture of ether-ammonia saturated methanol 96%+4%.

Fractions of 10 ml are collected and tested by t.l.c. The used developer was ninhydrine (amino-acids) or ceric (alkaloids).

When the excess amino-acid have undergone elution (ninhydrine-), more elution agent is used before switching to a mixture 92%-8%.

The amino-acid derivative of the alkaloids is then collected (ceric +).

Identical fractions are combined, dry evaporated (rotavapor), dissolved in methylene chloride, dried on $Na_2SO_4$, filtrated and evaporated to dryness. The foam which is obtained is the amino-acid derivative of the dimeric alkaloid, of which physico-chemical properties will be determined on aliquot parts. The remaining will be directly converted into a sulphate. Yield of the base of the various compounds are only indicative and may be improved.

Preparation of the sulphate

The amorphous base (foam) is dissolved in 20 times its weight of ethanol.

To this solution, very slowly and under fast stirring, two equivalents of sulfuric acid are added as a solution 2% sulfuric acid/98% anhydrous ethanol. (0.484 equivalent/liter). After two equivalents have been added, and ½ hour of stirring, concentration under reduced pressure takes place. By adding sulfuric ether, under fast stirring, the sulphate of the initial compound precipitates. After filtration and drying under reduced pressure at 10° C. the desired sulphate derivative is obtained, ready for use.

The numbering of the description of the MNR spectra in the following examples is inspired by the one proposed by Le Men and Taylor for derivatives of the aspidospermidine type (Experientia 21,508,1965).

EXAMPLE 1

Preparation of Vinblastine (VLB) base

To a solution of 1.5 g VLB sulphate ($1.65.10^{-3}$M) in 15 ml distilled water, under violent stirring, 15 ml methylene chloride and 1.5 ml conc. ammonia were successively added. After 5 minutes the mixture is decanted and the aqueous phase is further extracted by 3×15 ml methylene chloride. The combined organic phases are washed by 2×40 ml deionized water, dried on $Na_2SO_4$ and dry evaporated on rotavapor. 1.32 g of VLB base (99%) was obtained.

Preparation of 3-decarbomethoxy-O-4-deacetyl-vinblastin-3-carbohydrazide (VLH)

To a solution of 1 g vinblastine base ($1.23\ 10^{-3}$M) dissolved in 7 ml anhydrous ethanol, 14 ml anhydrous hydrazine and 7 ml anhydrous ethanol were added. The reaction mixture is then heated at 60° C. during 24 hours.

After cooling, 28 ml salt saturated water was added and extraction with the same volume of methylene chloride until a negative Meyers reaction is obtained on the acidified aqueous phase. The combined organic phases are dried with $MgSO_4$ and evaporated to dryness under reduced pressure.

The hydrazide which is obtained with a 88% yield (0,706 g) produced a single spot by t.l.c.

EXAMPLE 2

Preparation of ethyl N-(O-4-deacetyl-vinblastin-23-oyl)-L-leucinate (VLE)

To a solution of 275 mg ($3.58\ 10^{-4}$M) of O-4-deacetyl-vinblastine hydrazide in 7 ml anhydrous methanol and 20.5 ml 1N HCl, after cooling the solution at 0° C., 58 mg of sodium nitrite are added. After stirring for 25 minutes, the pH is adjusted to 8,5 by addition of an appropriate amount of a solution of 5% $NaHCO_3$. The azide which has been formed is extracted with methylene chloride. The organic phase is dried over $MgSO_4$ and filtrated. 68.4 mg ethyl L-leucinate ($4.29\ 10^{-4}$M was added and the solution is concentrated under reduced pressure to about 4 ml. The solution is allowed to stand in a refrigerator for 24 hours.

The reaction being then completed, 50 ml methylene chloride are added and the solution is washed several times with volumes of deionized water equal to the volume of the solution and one time with a NaCL saturated solution.

The combined organic phases are dried on $MgSO_4$, filtrated and evaporated to dryness.

300 mg of crude product are thus obtained to which 0.035 g $H_2SO_4$ in solution in 1 ml anhydrous methanol are added.

The salt which is obtained in precipitated by ether and the precipitate is washed 10 times with 50 ml anhydrous sulfuric ether.

183 mg (57%) of the product are thus obtained which is substantially pure and containing no ethyl leucinate.

After freeing of the bases, they may undergo a silica-gel chromatography (10 g $SiO_2$) and elution with 50 ml ether MeOH-$NH_3$ sat (92%/8% and then 250 ml ether/MeOH-$NH_3$ sat (85%/15%). VLE is obtained as head of the second eluate. 49% of VLE i.e. 152 mg base was thus collected.

Physico-chemical properties of VLE

Melting point: 169° C.
$[\alpha]_{Dc=0.35}^{CHCl_3}$: 60°.

UV spectrum (MeOH, $\lambda$max, nm, log$\epsilon$):
221 (4.62); 267 (4.15); 287 (4.02); 295 (3.99).
IR spectrum (KBr, $cm^{-1}$): 3470, 2960, 2880, 1735, 1665, 1619.
Mass spectrum (m/e, %): 924 (6) $M^+ +28$; 910 (56) $M^+ +14$; 897 (62); 896 (100); 865 (25); 938 (68); 772 (19); 709 (25); 651 (43); 571 (69).
NMR spectrum ($H^1$, $CDCl_3$, ppm, 360 MHz): 9.66 (1H, bs, $C^{16}$-OH); 8.20 (1H,s,$N'^{\alpha}$H); 7.52 (1H,d); 7.15 (3H,m); 6.56 (1H,s,$C^9$-H); 6.05 (1H,s,$C^{12}$-H); 5.86 (1H,dd,$C^{14}$-H, J 14-15-12 J14-3=3.6; 5.78 (1H,d,$C^{15}$-H); 4.69 (1H,m,CH(NHR)CO—); 4.2 (2H,q,OCH$_2$ CH$_3$); 4.18 (1H,t,$C^{17}$-H); 3.77 (3H,s,$OCH_3$); 3.66 (3H,s,$OCH_3$); 3.47 (1H,s,$C_5$-H); 2.77 (3H,s,$N^{\alpha}$-$CH_3$); 0.92 (12H,m,-$C^{18}H_3+C^{18'}H_3$+isopropyl).

EXAMPLE 3

Methyl N-(O-4-deacetyl-vinblastin-23-oyl)-L-leucinate (VLM)

Following the general procedure at page 30 VLM has been obtained with a 68% yield.

Physico chemical properties of VLM

Melting point: ~172° C.
$[\alpha]_{Dc=0.27}^{CHCl_3}$: ~67°.
UV Spectrum ($CH_3OH$, $\lambda$max, nm, log$\epsilon$): 220 (4.61); 267 (4.15); 287 (4.03); 294 (3.98).
IR Spectrum (KBr, $cm^{-1}$): 3475; 2960; 2880; 1740; 1680; 1615.
Mass spectrum (m/e, %): 910 (25) $M^+ +28$; 896 (78) $M^+ +14$; 883 (26) $M^+ +1$; 882 (36) $M^+$; 850 (29); 836 (41); 822 (100); 708 (15); 681 (56); 650 (78); 570 (70).
NMR spectrum ($CDCl_3$, ppm, 60 MHz): 9.21 (1H,s,$C^{16}$-OH); 8.1 (1H,s,$N'^{\alpha}$-H); 7.53 (1H,m); 7.23 (3H,m); 6.63 (1H,s,$C^9$-H); 6.13 (1H,s,$C^{12}$-H); 5.86 (2H,m,$C^{14}$-H+$C^{15}$-H); 3.83 (3H,s,—$OCH_3$); 3.80 (3H,s,—$COOCH_3$); 3.63 (3H,s,—$OCH_3$); 2.8 (3H,s,—$N^{\alpha}$—$CH_3$); 0.96 (12H,m,$C^{18}H_3+C^{18'}H_3$+isopropyl).

EXAMPLE 4 n-Butyl N-(O-4-deacetyl-vinblastin-23-oyl)-L-leucinate (VLn-But)

Following the general procedure at page 33, VLn-But has been obtained with a 58% yield.

Physico chemical properties of VLn-But

Melting point: ~158° C.

$[\alpha]_{Dc=0.26}^{CHCl_3}$: ~74°.

UV spectrum (CH$_3$OH, λmax, nm, logε): 200 (4.66); 266 (4.21); 289 (4.08); 296 (4.03).

IR spectrum (KBr, cm$^{-1}$): 3470, 2960, 2880, 1740, 1670, 1615.

Mass spectrum (m/e, %): 952 (5) M$^+$+28; 938 (31) M$^+$+14; 924 (12) M$^{30}$; 923 (15 M$^+$−1; 891 (13); 863 (36); 835 (5); 821 (11); 708 (33); 650 (81); 570 (100).

NMR spectrum (CDCl$_3$, ppm, 60 MHz): 9.6 (1H,s,C$^{16}$-OH); 8.06 (1H,s,N$^{'\alpha}$-H); 7.5 (1H,m); 7.2 (3H,m); 6.63 (1H,s,C$^9$-H); 6.1 (1H,s,C$^{12}$-H) 5.86 (2H,m,C$^{14}$-H+C$^{15}$-H); 4.2 (2H,t,—COO—CH$_2$); 3.83 (3H,s,—OCH$_3$); 3.63 (3H,s,—OCH$_3$); 2.8 (3H,s,—N—CH$_3$); 1 (15H,m,—C$^{18}$H$_3$+C$^{18}$H$_3$; CH$_3$ butyl; CH$_3$ isopropyl).

EXAMPLE 5

Octyl N-(O-4-deacetyl-vinblastin-23-oyl)-L-leucinate (VL-octyl)

Following the general procedure at page 30 VL-octyl has been obtained with a 48% yield.

Physico chemical properties of VL-Octyl

Melting point: ~145° C.

$[\alpha]_{Dc=0.33}^{CHCl_3}$: ~54°.

UV spectrum (CH$_3$OH, λmax, nm, log ε): 8.62 mg/l; 217 (4.69 ); 265 (4.14); 289 (4.01); 295 (3.95).

IR spectrum (KBr, cm$^{-1}$): 3460; 2940; 2920; 2870; 1735; 1665; 1610; 1500; 1455.

NMR spectrum (CDCl$_3$, ppm, 60 MHz): 9.6 (1H,s,C$^{16}$-OH); 8.1 (1H,s,N'-H); 7.55 (1H,m); 7.23 (3H,m); 6.5 (1H,s,C$^9$-H); 6.12 (1H,s,C$^{12}$-H); 5.90 (2H,m,C$^{14}$-H+C$^{15}$-H); 4.2 (2H,t,—O—CH$_2$—Oct; 1H,d,C$^{17}$-H); 3.83 (3H,s,—COOCH$_3$); 3.67 (3H,s,—OCH$_3$); 3.56 (1H,s,C$^5$-H); 2.83 (3H,s,N-CH$_3$); 1.33 (1OH, m, massif octyl+CH$_2^{19'}$+CH$_2^{19}$); 1 (15H,m massif octyl+CH$_3^{18}$+CH$_3^{18'}$).

EXAMPLE 6

Ethyl N-(O-4-deacetyl-vinblastin-23-oyl)-D-leucinate (VDLE)

Following the general procedure at page 30 VDLE has been obtained with a 74% yield.

Physico-chemical properties of VDLE:

Melting point: ~181° C.

$[\alpha]_{Dc=0.28}^{CHCl_3}$: ~70°.

UV spectrum (methanol, λmax, nm, logε): 220 (4.67); 226 (4.20); 288 (4.11); 295 (4.02).

IR spectrum (KBr, cm$^{-1}$): 3460; 2960; 2880; 1735; 1665; 1605.

Mass spectrum (m/c %): 924 (14) M$^+$+28; 910 (32); M$^+$+14; 897 (38) M$^+$+1; 896 (66) M$^+$; 863 (28); 835 (43); 709 (43); 651 (81); 570 (100).

NMR spectrum (CDCl$_3$, ppm, 60 MHz): 9.6 (1H,s,C$^{16}$-OH); 8.16 (1H,s,N$^{'\alpha}$-H); 7.66 (1H,m); 7.26 (3H,m); 6.7 (1H,s,C$^9$-H); 6.16 (1H,s,C$^{12}$-H); 5.90 (2H,m,C$^{14}$-H+C$^{15}$-H); 4.26 (2H,q,—COOCH$_2$); 3.83 (3H,s,—OCH$_3$); 3.66 (3H,s,—OCH$_3$); 290 (3H,s,—N$^\alpha$—CH$_3$); 1.3 (3H,t,—COOCH$_2$)—CH$_3$; 0.96 (12H,m,C$^{18'}$H$_3$+C$^{18}$H$_3$+isopropyl).

EXAMPLE 7

Ethyl N-(O-4-deacetyl-vinblastin-23-oyl)-L-serinate (VSE)

Following the general procedure at page 30 VSE has been obtained with a 35% yield.

Physico-chemical properties of VSE $[\alpha]_{Dc=0.7}^{CHCL_3}$: ~65°.

UV spectrum MeOH, λmax, nm, logε): 215 (4.76); 266 (4.31); 288 (4.20); 297 (4.15).

IR spectrum (CHCl$_3$, cm$^{-1}$): 3460; 3400; 2965; 2935; 2880; 1730; 1665; 1605.

NMR spectrum (CDCl$_3$, ppm, 60 MHz): 8.13 (1H,s,N$^{\alpha'}$-H); 7.9 (1H,d,—OH); 7.52 (1H,m); (7.20 (3H,m); 6.63 (1H,s,C$^9$-H); 6.1 (1H,s,C$^{12}$-H); 5.9 (2H,m,C$^{14}$-H+C$^{15}$-H); 4.3 (2H,g,—COO—CH$_2$—); 3.83 (3H,s,—OCH); 3.66 (3H,s,—OCH$_3$); 2.67 (3H,s,—N$^\alpha$—CH$_3$); 1.34 (3H,t, (—COO—CH$_2$)Ch$_3$); 0.95 (6H,m,C$^{18'}$H$_3$+C$^{18}$H$_3$).

EXAMPLE 8

Ethyl N-(O-4-deacetyl-vinblastin-23-oyl)-L-glutamate (VGE)

Following the general procedure at page 30 VGE has been obtained with a 55% yield.

Physico-chemical properties of VGE

Melting point: ~149° C.

$[\alpha]_{Dc=2}^{CHCl_3}$: ~59°.

UV spectrum (MeOH, 10 mg/l, λmax, nm, log ε): 219 (4.46); 269 (3.94); 288 (3.80); 2.96 (3.76).

IR spectrum (KBr, cm$^{-1}$): 3460; 3395; 2960; 2920; 2870; 1730; 1665; 1610; 1500.

NMR spectrum (CDCl$_3$, ppm, 60 MHz): 9.63 (1H,s,,C$^{16}$-OH); 8.10 (1H,s,N$^{\alpha'}$-H); 7.6 (1H,m); 7.16 (3H,m); 6.64 (1H,s,C$^9$-H); 6.07 (1H,s,C$^{12}$-H); 5.83 (2H,m,C$^{14}$H—C$^{15}$H); 4.23 (2H,q,—COOCH$_2$—); 4.16 (2H,q,—COOCH$_2$—); 3.8 (3H,s,—OCH$_3$); 3.64 (3H,s,—OCH$_3$); 3.5 (1H,s,C$^5$-H); 2.8 (3H,s,—N$^\alpha$CH$_3$); 1.33 (3H,t,—CH$_3$); 1.26 (3H,t,—CH$_3$); 1 (6H,m,C$^{18}$H$_3$+C$^{18'}$H$_3$).

EXAMPLE 9

Ethyl N-(O-4-deacetyl-vinblastin-23-oyl)-L-phenylalinate (VPE)

Following the general procedure at page 30 VPE has been obtained with a 66% yield.

Physico-chemicalo properties of VPE

Melting point: ~154° C.

$[\alpha]_{Dc=1.2}^{CHCl_3}$: ~78°.

UV speectrum (MeOH, 9.8 mg/l, λmax, nm, logε): 217.5 (4.67); 265 (4.13); 286.5 (3.99); 295.5 (3.95).

IR spectrum (KBr, cm$^{-1}$): 3560; 3460; 3400; 2860; 2830; 1730; 1650; 1610; 1500; 1455.

Mass spectrum (m/c %): 958 (17); 944 (41); 930 (35); 871 (64); 651 (41); 588 (41); 571 (53); 401 (100).

NMR spectrum (CDCl$_3$, ppm, 36 MHz) 9.48 (1H,bs,—C$^{16}$—OH); 8.1 (1H,s,N$^{\alpha'}$-H); 7.6 (1H,d); 7.5 (1H,d); 7.3-7.02 (7H,m); 6,6 (1H,s,C$^9$-H); 6.1 (1H,s,C$^{12}$-H); 5.87 (2H,m,C$^{14}$-H+C$^{15}$-H) (J$^{15-14}$=12 Hz; J$^{14-3}$=8.6 Hz); 4.49

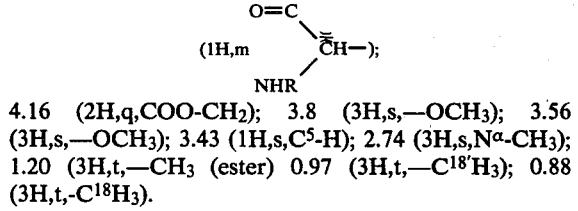

4.16 (2H,q,COO-CH₂); 3.8 (3H,s,—OCH₃); 3.56 (3H,s,—OCH₃); 3.43 (1H,s,C⁵-H); 2.74 (3H,s,Nα-CH₃); 1.20 (3H,t,—CH₃ (ester) 0.97 (3H,t,—C¹⁸'H₃); 0.88 (3H,t,-C¹⁸H₃).

EXAMPLE 10

Methyl N-(O-4-deacetyl-vinblastin-23-oyl)-L-isoleucinate (VILM)

Following the general procedure at page 30 VILM has been obtained with a 66% yield.

Physico-chemical properties of VILM $[\alpha]_{Dc=0.135}^{CHCl_3}$ ~66°.

UV spectrum (MeoH, λ max, nm,log ε,): 225 (4.55); 266 (4.18); 288 (4.05); 295 (4.00).

NMR spectrum (CDCl₃, 360 MHz): 9.48 (bs,1H,C¹⁶-OH); 8.03 (s,1H,NH); 7.51 (m,2H); 7.23-7.06 (m,2H); 6.58 (s,1H,C⁹-H); 6.20 (s,1H,C¹²-H); 5.85 (dd, 1H,C¹⁴-H; J¹⁵⁻¹⁴=12 Hz; J¹⁴⁻³=3,6 Hz); 5.78 (d,1H,C¹⁵-H); 4.62

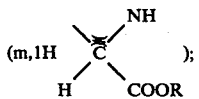

4.17 (d,1H); 3.77 (s,3H,COOCH₃); 3.75 (s,3H); 3.6 (s,3H); 2.73 (s,3H,Nα-CH₃); 2.58 (s,1H,C²¹ -H); 0.92 (m,12H,C¹⁸H₃-C¹⁸'H).

EXAMPLE 11

Ethyl N-(O-4-deacetyl-vinblastin-23-oyl)-L-tyrosinate (V-Tyr E)

Following the general procedure at page 30 V-Tyr E has been obtained with a 48% yield.

Physico-chemical properties of V-Tyr E $[\alpha]_{Dc=0.1087}^{CHCl_3}$ ~64°.

UV spectrum (CH₃OH, λmax, nm, log ε): 227 (4.73); 266 (4.26); 288 (4.07); 296 (3.94).

IR spectrum (Kbr, cm⁻¹): 3460, 3400, 3040, 2950, 2840, 1715, 1660, 1610, 1500, 1455, 1225.

NMR spectrum (360 MHz): 9.6 (bs,1H,C¹⁶-OH); 8.05 (s,1H,NH); 7.55 (m,2H); 7.21-7.06 (m,2H); 7.03 (d,2H, arom tyr J=7.5); 6.7 (d,2H,arom tyr.J=7.5); 6.55 (s,1H,C⁹-H); 6.05 (s,1H,C¹²-H); 5.83 (dd,1H,C¹⁴-H); J¹⁵⁻¹⁴=12 Hz; J¹⁴⁻³=3.6 Hz); 5.76 (d,1H, C¹⁵-H); 4.83 (m,1H,CH); 4.13 (massif 3H,—COOCH₂,C¹⁷-H); 3.76 (s,3H); 3.6 (s,3H); 3.45 (s,1H,C⁵-H); 2.71 (s,3H,-Nα-CH₃); 1.21 (t,3H,—CH₃—(CH₂OOC)); 0.88 (m,6H,—C¹⁸H₃—C¹⁸'H₃).

EXAMPLE 12

Ethyl N-(O-4-deacetyl-vinblastin-23-oyl)-L-tryptophanate (V-Trypt E)

Following the general procedure at page 30 V-Trypt E has been obtained with a 72% yield.

Physico-chemical properties of V-Trypt E $[\alpha]_{Dc=0.51119}^{CHCl_3}$: ~90°.

UV spectrum (MeOH, λ max, nm, log ε): 225 (5.15); 267 (4.65); 280 (ep); 290 (4.55).

Mass spectrum (m/e %) Isobutane molecular ionisation 998 (M⁺+1+28), 984 (M⁺+1+14), 970(M⁺+1), 926 C₅₆H₆₈N₆O₉.

IR spectrum (KBr, cm⁻¹): 3460, 3400, 3040, 2960, 2940, 2880, 1725, 1660, 1610, 1500, 1455, 1225, 740.

NMR spectrum (CDCl₃, 360 MHz): 9.5 (1H,s,C¹⁶-OH); 8.2 (1H,s,NH,trypt); 8.03 (1H,s,NH); 7.66 (1H,d,trypt; J=7.2 Hz); 7.58 (1H,d,trypt; J=7.2 Hz); 7.51 (1H,d,trypt; J=7.2 Hz); 7.31 (1H,d,trypt; J=7.2 Hz); 7.25-7.04 (5H,m); 6.58 (1H,s,C⁹ -H); 6.06 (1H,s,c¹² -H); 5.83 (1H,dd,C¹⁴-H; J=12 Hz; J=3 6 Hz); 5.78 (1H,d,C¹⁵ -H; J=12 Hz); 4,95 (1H,q,>CH); 3.75 (3H,s,—COOCH₃); 3.6 (3H,s,—OCH₃); 3.4 (1H,s,C⁵-H); 2.77 (1H,s,N-CH₃); 1.15 (3H,t—COOCH₂ (CH₃)).

EXAMPLE 13

Methyl N-(O-4-deacetyl-vinblastin-23-oyl)-L-tryptophanate (V-Trypt M)

Following the general procedure at page 30 V-Trypt M has been obtained with a 41% yield.

Physico-chemical properties of V-Trypt M $[\alpha]_{Dc=1.82}^{CHCl_3}$: ~94°.

UV spectrum (MeOH, λ max, nm, log ε): 269 (4.48); 280; 289 (4.32).

IR spectrum (KBr, cm⁻¹): 1730, 1710, 1660, 1610, 1495, 1455, 1220, 740.

NMR spectrum (260 MHz): 9.5 (1H,bs,C¹⁶-OH); 8.06 (1H,s,NH ind); 8.01 (1H,s,NH ind); 7.65 (1H,d); 7.58 (1H,d); 7.38-7.06 (7H,m); 6.41 (1H,s,C⁹-H); 6.05 (1H,s,C¹²-H); 5.85 (1H,dd,C¹⁴-H); J=12 Hz; J'=3.6 Hz); 5.78 (1H,d,C¹⁵-H;J=12 Hz); 4.95 (1H, q,); 4.2 (1H,m,C¹⁷-H); 3.75 (3H,s,—OCH₃); 3.61 (3H,s,—COOCH₃); 3.58 (3H,s,—COOCH₃); 3.43 (2H,s,C⁵-H); 2.6 (3H,s,N-CH₃).

EXAMPLE 14

Ethyl N-(O-4-deacetyl-vinblastin-23-oyl)-L-valinate (VVE)

Following the general procedure at page 30 VVE has been obtained with a 63% yield.

Physco-chemical properties of VVE

UV spectrum (MeOH, λ max, nm, log ε): 226 (4.95); 267 (4.57); 285 (4.45); 296 (4.40).

Mass spectrum (m/e %): 910 (0,1); 896 (2); 882(5); 823(4.5); 822(6); 708(5.3); 653(9.2); 651(8.7); 650(14.6); 572(8.7); 571(23.3); 539 (10.7); 355(16); 354(10); 353(31); 294(17); 188(8.5); 156(100); 155(11.8); 154(11.3); 144(12.2); 141(12.1); 140(16.4); 136(13); 135(20.4); 124(61); 122(35,5); 121(15.3).

IR spectrum (KBr, cm⁻¹): 3540, 3470, 3420, 2960, 2930, 2870, 1730, 1720, 1670, 1610, 1500, 1455, 1225, 745.

NMR spectrum: 9.48(1H,bs,C¹⁶-OH); 8.03 (1H,bs,NH ind); 7.55 (1H,d;J=7.2 Hz); 7.51 (1H,d,J=7.2 Hz); 7.51 (1H,d); 7.23-7.06 (3H,m); 6.58 (1H,s,C⁹-H); 6.06 (1H,s,C¹²-H); 5.85 (1H,dd,C¹⁴-H; J¹⁴⁻¹⁵=12 Hz; J¹⁴⁻³=3.6 Hz); 5.78 (1H,d,C¹⁵-H; J=12 Hz); 4.56 (1H,dd,C); 4.21 (2H,q,COOCH₂); 4.15 (1H,d,C¹⁷-H); 3.96 (1H,t); 3.76 (3H,s,OCH₃); 3.6 (3H,s, COOCH₃);

3.46 (1H,s,$C^5$-H); 2.73 (3H,s,N-CH$_3$); 1.31 (6H,m,COOCH$_2$CH$_3$); 0.96 (14H,m); 0.9 (14H,t).

EXAMPLE 15

Ethyl N-(O-4-deacetyl-vinblastin-23-oyl)-L-iso-leucinate (VILE)

Following the general procedure at page 30 VILE has been obtained with a 58% yield.

Physico-chemical properties of VILE

UV spectrum (MeOH, λ max, nm, log ε): 226 (4.94); 266 (4.56); 285 (4.44); 295 (4.38).

Mass spectrum (m/e %) 924 (7);910(11); 897(23); 896(44.4); 867(11,3); 837(18.7); 836(26.6); 822(4); 709(10); 650(21); 571(13); 570(34.7); 366(21.7); 154(100); 126(11).

IR spectrum (KBr, cm$^{-1}$): 3460,3440,3040,2960, 2940, 2880, 1730, 1665, 1610, 1500, 1455, 1225, 745.

NMR spectrum (CDCl$_3$, 360 MHz): 9.46(1H,bs,$C^{16}$-OH); 8.03(1H,bs,NH); 7.55(1H,d;J=7.2 Hz); 7,51(1H,d); 7.23-7.06 (3H,m); 6.58 (1H,s,$C^9$ -H); 6.06 (1H,s,$C^{12}$ -H); 5.85 (1H,dd,$C^{14}$ -H; J=12 Hz;J'=3,6 Hz); 5.78 (1H,d,$C^{15}$ -H); J=12 Hz); 4.61 (1H,q(dd),$\tilde{C}$); 4.21 (2H,q,COO—CH$_2$—); 4.15 (1H,d,$C^{17}$ -H); 3.96 (1H,t); 3.76 (3H,s,OCH$_3$ ester 3.6 (3H,s,OCH$_3$); 3.46 (1H,s,$C^5$ -H); 2.73(3H,s,N-CH$_3$); 1.25 (3H,t,COOCH$_2$CH$_3$).

EXAMPLE 16

Ethyl N-(O-4-deacetyl-vinblastin-23-oyl)-D-tryptophanate (VD Trypt E)

Following the general procedure at page 30 VD Trypt E has been obtained with a 69% yield.

Physico-chemical properties of VD Trypt E $[\alpha]_{Dc=0.3295}^{CDCl3}$: 70°.

UV spectrum (MeOH, λmax,nm, logε): 225 (4.77); 269 (4.30); 290 (4.20); 320 (ep).

Mass spectrum (m/e %): 970, 391, 279, 165, 108, 35.

IR spectrum (KBr, cm$^{-1}$): 3460, 3400, 3050, 2960, 2940, 2870, 1735, 1665, 1610, 1495, 1455, 1210, 740.

NMR spectrum: 9.53 (1H,bs,$C^{16}$-OH); 8.1 (1H,s,NH ind tryp); 8.02 (1H,s,NH ind); 7.76 (1H,d); 7.65 (1H,d); 7.51 (1H,d); 7.35 (1H,d); 7.2-7.05 (6H,m); 6.53 (1H,s,$C^9$H); 5.98 (1H,dd,$C^{14}$H J$^{14\text{-}15}$=12 Hz,J'$^{14\text{-}3}$=3.6 Hz); 5.73 (1H,d,$C^{15}$-H; J=12 Hz); 4.86 (1H,q,C-); 4.1 (3H,m,$C^{17}$-H-COOCH$_2$); 3.75 (3H,s,COOCH$_3$); 3.6 (3H,s,—OCH$_3$); 3.33 (2H,s,$C^5$-H); 2.43 (3H,s,N-CH$_3$); 1.16 (3H,t,—COOCH$_2$—CH$_3$); 0.93 (8H,m).

EXAMPLE 17

Ethyl N-(O-4-deacetyl-vinblastin-23-oyl)-L-valyl-L-tryptophanate (V-Val-Trypt-E)

Following the general procedure at page 30 V-Val-Trypt E has been obtained with a 40% yield.

Physico- chemical properties of V-Val-Trypt-E $[\alpha]_{Dc=0.3589}^{CHCl3}$: 36°.

UV spectrum (methanol, λ max, nm, log ε): 270 (4.42); 290; 312 (4.96).

IR spectrum (KBr, cm$^{-1}$): 3480, 3400, 2960, 2940, 2870, 1735, 1725, 1660, 1610, 1500, 1455, 1230.

NMR spectrum (CDCl$_3$, 360 MHz): 9.5 (1H,bs,$C^{16}$-OH); 8.18(1H,s,NH ind); 8.01 (1H,s,NH ind); 7.6-7.06 (10H,m,arom); 6.41 (1H,s,$C^9$ -H); 5.95(1H,s,$C^{12}$ -H); 5.85 (1H,dd,$C^{14}$ -H; J$^{15\text{-}14}$=12 Hz; J$^{8\text{-}14}$=3,6 Hz); 5.75 (1H,d,$C^1$-H; J$^{15\text{-}14}$=12 Hz); 5.02 (1H,m,$\tilde{C}$); 4.9 (1H,m,C); 3,73 (3H,s,COOCH$_3$); 3.56 (3H,s,—OCH$_3$); 3.43 (2H,s,$C^5$ -H); 2.61 (3H,s,N-CH) 1.05-0.86 (±16H,m,CH$_3$).

EXAMPLE 18

Ethyl N-(O-4-deacetyl-vinblastin-23-oyl)-L-leucyl-L-alanyl-L-leucyl-L-alanylate (V-Leu-Ala-Leu-Ala-E)

In accordance with the general procedure and preparing the azide from 700 mg monohydrazide, the reaction with 377 mg ethyl-L-Leu-L-Ala-L-Leu-L-Alaninate at 4° C. for 60 h yields 213 mg pure V-Leu-Ala-Leu-Ala-E. The purification is effected by passing the crude product first on a column of silica 60 Merck (230 mesh) using as eluant a mixture ether-MeOH sat NH$_3$ (86:14), then on an identical column using as eluant a mixture of isopropanol-ethyl-acetatecyclohexane (40:20:40).

Physico-chemical properties of V-Leu-Ala-Leu-Ala-E

UV spectrum (methanol, 5.74 mg/100 cc, log ε): 266 (4.24); 285-288 (4.12); 296 (4.07).

Mass spectrum (isobutane DCI, molecular ionisation) 1152 (M$^+$+1), 1166 (M$^+$+1+14), 1134, 1108, 1094.

IR spectrum (KBr): 3400, 2960, 1740, 1660, 1620, 1506, 1460, 1225, 745 cm$^{-1}$.

NMR spectrum (CDCl$_3$, 360 MHz, ppm): 0,91, 1,27 (t), 1,40 (2d), 1,67 (dxd), 2.61 (s), 2.72 (s) 3.60 (s), 3,75(s), 4.19 (q), 5.74 (d), 5.83 (dxd), 6.03 (s,) 6.59 (s), 6.88 (d), 7.00(d), 7.39(d), 7.49 (d), 7.53 (d) 8.02 (s), 9.57 (s).

EXAMPLE 19

Ethyl-N-(O-4-deacetyl-vinblastin-23-oyl-L-tryptophyl-L-tryptophanate (V-Tryp-Tryp-E)

In accordance with the general procedure and using 1 g hydrazide and 543 mg ethyl L-tryptophyl-L-tryptophanate, 268 g of pure V-Tryp-Tryp-E was obtained by passing the crude product on a column of silica using as eluant first a mixture ether-methanol sat. NH$_3$ (92:8) then an identical mixture but in a ratio 86:14.

Physico-chemical properties of V-Tryp-Tryp-E

UV spectrum (MeOH): max 272 (4.38); 278 (4.37); 290 (4.31); (49,6 mg/l) min 248 (4.18), 288 (4.30)

Mass spectrum: DCI isobutane; 1184, 1170; 1156 (M$^+$+1); 1112; 1098; 624; 498; 165.

IR spectrum (Kbr) 3410; 2970; 2880; 1725; 1665; 1615; 1500; 1460; 1230 cm$^{-1}$.

EXAMPLE 20

Ethyl N-(O-4-deacetyl-vinblastin-23-oyl)-L-tryptophylglycinate (V-Tryp-Gly-E)

Condensation of 596 mg hydrazide and 226 mg ethyl L-tryptophylglycinate (41h, 4° C.) give 200 mg V-Tryp-Gly-E, after purification on a silica column using as eluant a mixture ether-methanol wherein the proportion of CH$_3$OH-NH$_3$ is increased from 4 to 14%.

Mass spectrum (molecular ionisation with isobutane): M$^+$+1 1027, 1042, 1055, 1013, 983, 969.

EXAMPLE 21

Ethyl N-(O-4-deacetyl-vinblastin-23-oyl)-L-valinyl-L-tryptophanate (V-Val-Tryp-E)

From 500 mg hydrazide of deacetyl-VLB and 215 mg ethyl L-valinyl-L-tryptophanate, 215 mg pure V-Val-Tryp-E have been obtained after column chromatography.

Mass spectrum (molecular ionisation $NH_3$): $M^+ + 1$ 1069, 632, 617, 498, 332, 223.

EXAMPLE 22

Ethyl N- (vinblastin-23-oyl)-L-valinate

Ethyl N-(O-4 deacetyl vinblastin-23-oyl-L-valinate (100 mg) were reacted with a mixture of pyridine (2.5 mL), acetic anhydride (2.5 mL) under inert atmosphere and stirring for 24 h. After adding methanol and concentration under reduced pressure the product was dissolved in dichloromethane and washed with NaCl sat.water. The organic phase was dried on $Na_2SO_4$ and concentrated under reduced pressure. The product was purified by t.l.c. using as eluant a mixture isopropanol-/ethylacetate/cyclohexane (40/20/40). 29 mg of ethyl N-(vinblastin-23-oyl)-L-valinate was thus obtained.

Mass spectrum (molecular ionisation isobutane): $M^+ + 1$ 925; $M^+ + 1 + 14$ 939; $M^+ + 1 + 28$ 953; 924; 907; 893; 882; 881; 867; 866; 392; 279.

IR spectrum (KBr, $cm^{-1}$): 3480, 3430, 2970, 1740, 1690, 1615.

UV spectrum (54,2 mg/L, $\lambda$ max, log $\epsilon$): 263 (4.28); 288 (4.17); 296 (4.13).

We claim:

1. A vinblastine derivative of the formula

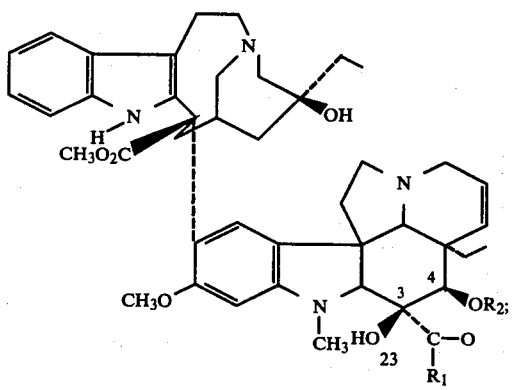

wherein $R_1$ is an ester of a α-aminoacid selected from the group consisting of glycine, alanine, valine, leucine, isoleucine, serine, threonine, aspartic acid, glutamic acid, aspargine, glutamine, arginine, lysine, cysteine, cystine, methionine, phenylalanine, tyrosine, tryptophan, proline, histidine, hydroxy-lysine, hydroxyproline, or of a peptide consisting of 1-6 identical or different such amino-acids, and the ester group, which may be straight or branched, being a carboalkoxy group having 2-9 carbon atoms, and $R_2$ is hydrogen or a $C_2$-$C_9$ alkanoyl group, and their pharmaceutically acceptable mineral or organic acid addition salts.

2. A vinblastine derivative of the formula

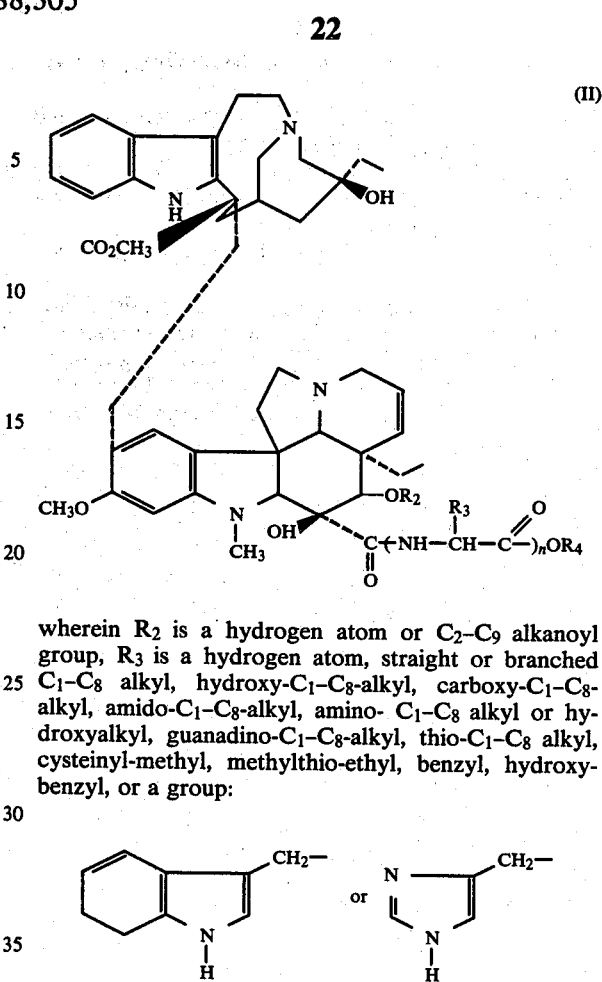

wherein $R_2$ is a hydrogen atom or $C_2$-$C_9$ alkanoyl group, $R_3$ is a hydrogen atom, straight or branched $C_1$-$C_8$ alkyl, hydroxy-$C_1$-$C_8$-alkyl, carboxy-$C_1$-$C_8$-alkyl, amido-$C_1$-$C_8$-alkyl, amino- $C_1$-$C_8$ alkyl or hydroxyalkyl, guanadino-$C_1$-$C_8$-alkyl, thio-$C_1$-$C_8$ alkyl, cysteinyl-methyl, methylthio-ethyl, benzyl, hydroxybenzyl, or a group:

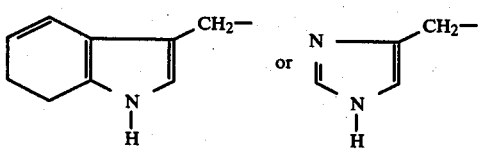

or $R_3$ together with the carbon to which it is attached and the amido nitrogen, forms an azole or an hydroxyazole ring; n is an integer of from 1 to 6, and $R_4$ is a straight or branched $C_1$-$C_8$-alkyl, or a benzyl group and their pharmaceutically acceptable mineral and organic acid addition salts.

3. Ethyl or methyl N-(O-4-deacetyl-vinblastin-23-oyl)-L-tryptophanate and their additions salts with pharmaceutically acceptable acids.

4. Ethyl or methyl N-(O-4-deacetyl-vinblastin-23-oyl)-isoleucinate and their addition salts with pharmaceutically acceptable acids.

5. Ethyl N-(O-4-deacetyl-vinblastin-23-oyl)-valinate and its addition salts with pharmaceutically acceptable acids.

6. Ethyl N-(O-4-deacetyl-vinblastin-23-oyl)-L-valyl-L-tryptophanate and its addition salts with pharmaceutically acceptable acids.

7. A compound in accordance with claim 2, wherein the addition salt is the 1:1 addition salt with sulfuric acid.

8. The sulfuric acid addition salt of a compound selected from the group consisting of:
   ethyl or methyl N-(O-4-deacetyl-vinblastin-23-oyl)-L-tryptophanate
   ethyl or methyl N-(O-4-deacetyl-vinblastin-23-oyl)-isoleucinate
   ethyl N-(O-4-deacetyl-vinblastin-23-oyl)-valinate
   ethyl N-(O-4-deacetyl-vinblastin-23-oyl)-L-valyl-L-tryptophanate
   wherein said addition salt is in a ratio of 1:1.

9. Ethyl N-(O-4-deacetyl-vinblastin-23-oyl)-L-tryptophanate sulphate.

10. A compound in accordance with claim 1 selected from the group consisting of:
Ethyl N-(O-4-deacetyl-vinblastin-23-oyl)-L-leucinate
Methyl N(O-4-deacetyl-vinblastin-23-oyl)-L-leucinate
n-Butyl N(O-4-deacetyl-vinblastin-23-oyl)-L-leucinate
Octyl N(O-4-deacetyl-vinblastin-23-oyl)-L-leucinate
Ethyl N(O-4-deacetyl-vinblastin-23-oyl)-D-leucinate
Ethyl N(O-4-deacetyl-vinblastin-23-oyl)-L-glutamate
Ethyl N(O-4-deacetyl-vinblastin-23-oyl)-L-serinate
Ethyl N(O-4-deacetyl-vinblastin-23-oyl)-L-tryptophanate
Methyl N(O-4-deacetyl vinblastin-23-oyl)-L-tryptophanate
Ethyl N(O-4-deacetyl vinblastin-23-oyl)-D-tryptophanate
Ethyl N(O-4-deacetyl-vinblastin-23-oyl)-L-alaninate
Ethyl N(O-4-deacetyl-vinblastin-23-oyl)-L-phenyl alaninate
Ethyl N(O-4-deacetyl-vinblastin-23-oyl)-L-isoleucinate
Methyl N(O-4-deacetyl-vinblastin-23-oyl)-L-isoleucinate
Ethyl N(O-4-deacetyl-vinblastin-23-oyl)-L-valinate
Ethyl N(O-4-deacetyl-vinblastin-23-oyl)-L-tyrosinate
Ethyl N(O-4-deacetyl-vinblastin-23-oyl)-L-valyl-L-tryptophanate
and their pharmaceutically acceptable mineral or organic acid addition salts.

11. Pharmaceutical composition for use in human or veterinary medicine for treating leukemia, solid tumors treatable with vinblastine, vincristine or vindesine or Hodgkins disease containing a compound in accordance with claim 2 in an amount of about 2–900 mg in a unitary dose.

12. Pharmaceutical composition for use in human or veterinary medicine for treating leukemia, solid tumors treatable with vinblastine, vincristine or vindesine or Hodgkins disease or Hodgkins disease containing a compound in accordance with claim 10 in an amount of about 2–900 mg in a unitary dose.

13. Pharmaceutical composition in accordance with claim 11 wherein the active compound is ethyl N(O-4-deacetyl-vinblastin-23-oyl)-L-tryptophanate and its addition salt with a pharmaceutically acceptable salt.

14. Pharmaceutical composition in accordance with claim 11 wherein the active compound is ethyl N(O-4-deacetyl-vinblastin-23-oyl)-L-valyl-L-tryptophanate and its addition salt with a pharmaceutically acceptable salt.

15. Pharmaceutical composition in accordance with claim 11 wherein the active compound is in a pharmaceutically acceptable diluent.

16. Pharmaceutical composition in accordance with claim 11 wherein the diluent is a sterile buffered aqeous solution.

17. The method of treating leukemia, solid tumors treatable with vinblastine, vincristine or vindesine or Hodgkins disease which comprises administering to a cancer patient in therapeutically effective amount, a compound as defined in claim 2.

* * * * *